US007337994B2

United States Patent
Tavares et al.

(10) Patent No.: US 7,337,994 B2
(45) Date of Patent: Mar. 4, 2008

(54) ROPE-ON-SPOOL UNCOILER AND GRANULATOR

(75) Inventors: Bruce Anthony Tavares, Hartland, WI (US); Frederick Emmett Coffey, Yardley, PA (US); Dennis Keith Rice, Quakertown, PA (US)

(73) Assignee: React-NTI, LLC, Lino Lakes, MN (US)

( * ) Notice: Subject to any disclaimer, the term of this patent is extended or adjusted under 35 U.S.C. 154(b) by 737 days.

(21) Appl. No.: 10/758,052

(22) Filed: Jan. 14, 2004

(65) Prior Publication Data

US 2004/0251340 A1 Dec. 16, 2004

Related U.S. Application Data

(63) Continuation-in-part of application No. 10/229,452, filed on Aug. 28, 2002, now Pat. No. 6,683,031, which is a continuation-in-part of application No. 09/861,842, filed on May 21, 2001, now Pat. No. 6,506,712.

(51) Int. Cl.
    *B02C 11/08* (2006.01)
(52) U.S. Cl. ........................... 241/34; 57/1 R
(58) Field of Classification Search ............ 241/34
    See application file for complete search history.

(56) References Cited

U.S. PATENT DOCUMENTS

| 3,735,661 | A | * | 5/1973 | Eichler et al. ................ 83/675 |
| 3,831,482 | A | * | 8/1974 | Eichler et al. ................ 83/675 |
| 4,028,779 | A | | 6/1977 | Shah |
| 4,459,093 | A | | 7/1984 | Asano |
| 6,325,322 | B1 | | 12/2001 | Lewis |
| 6,379,594 | B1 | * | 4/2002 | Dopfner et al. ............... 264/28 |
| 6,506,712 | B2 | * | 1/2003 | Tavares ...................... 508/216 |
| 6,683,031 | B1 | * | 1/2004 | Tavares ...................... 508/216 |

FOREIGN PATENT DOCUMENTS

EP 0 836 887 A 4/1998

* cited by examiner

*Primary Examiner*—Ellen M. McAvoy
(74) *Attorney, Agent, or Firm*—Alfred D. Lobo

(57) ABSTRACT

Rope made of cellulose fibers, the polymeric chemical structure of which fibers has not been modified (referred to as "raw" cellulose fibers), are subjected to intense electron beam irradiation insufficient to degrade their chemical structure but sufficient to modify their physical structure so as to allow them to be comminuted into fragments having a length no more than 6.35 mm (0.25"), preferably less than 3.175 mm (0.125"), and preferably 50% by weight of the fibers have a length less than 70 μm. Such fragments of fibers are found to be particularly susceptible to being micronized in a micronizer into elongated granular fragments smaller than about 20 μm at an economical production rate in excess of 22.7 Kg/hr (50 lb/hr) which was not possible when the micronizer was fed with naturally occurring fibers.

9 Claims, 4 Drawing Sheets

ROPE-ON-SPOOL UNCOILER AND GRANULATOR

CROSS-REFERENCE TO RELATED APPLICATIONS

This application is a continuation-in-part application of Ser. No. 10/229,452 ("the '452 application") filed 28 Aug. 2002 now U.S. Pat. No. 6,683,031 which is a continuation-in-part application of Ser. No. 09/861,842 filed 21 May 2001, issued as U.S. Pat. No. 6,506,712 ("the '712 patent") on 14 Jan. 2003.

FIELD OF THE INVENTION

The present invention relates to a system for uncoiling and committing a flexible cord of twisted cellulose fibers, referred to as "rope", into tiny fragments of the fibers forming the rope, without exerting so great a tension on the rope as to break it. Such fragments may be used to provide a low-density non-toxic filler in thermoformed synthetic resinous articles and as a bulking agent in cosmetics. The term "tiny fragments" is used to refer to fragments of cellulose fibers generated in a high-speed revolving blade chopper having a stationary adjustable bed blade.

BACKGROUND OF THE INVENTION

The aforementioned '712 patent teaches the irradiation of naturally occurring or raw plant material which provides fibers characterized by the growth of layers of cellulose building up cell walls. This growth of cellulose fibers occurs in farmed crops such as cotton, jute, hemp, sisal and the like, which are commonly used to make cordage and rope in a wide range of diameters and tensile strengths. Making rope requires twisting relatively short cellulose fibers of one or more of the foregoing naturally occurring fibers into yarn, then twisting multiple yarns into rope. Having expended the energy and cost to make rope it is self-evident that one would not go to the trouble and expense of making rope if one then deliberately intended to convert the rope into fibers.

As described in the pending '452 application, chopping a mass of cotton fibers into small squares in the range from 6.35 mm (0.25") to 12.7 mm (0.5") in length in a HOG or Cumberland chopper, and feeding the squares to a micronizer results in micronized particles having a narrow size range in which at least 90% by weight of the micronized particles are less than 10 μm in length, and the average length of all particles is in the range from about 4-5 μm. The '452 application also teaches that rope may be micronized after being first committed with an inline cutter having a rotary blade and six knives, a bed knife, a 22 HP motor and a custom feed tube with six 6 feed tubes each having a diameter of 19.05 mm (0.75"). The cutter motor is controlled by a variable frequency drive unit, and the rotary speed of the cutter and the lineal feed rate of the pinch roll feed unit determines the cut length of the fibers which is typically 6.35 mm (0.25"). The novel rope-on-spool uncoiler and granulator system disclosed herein can, if desired, provide chopped fibers in the same size range. However, this cut length of fibers is found to be too long to be fed to the micronizer, as are fibers 3.18 mm (0.125") or longer, if the micronizer is to produce more than 90% of the micron-sized fragments collected from its discharge in a critically small length less than 3.18 mm (0.125") at a production rate in excess of 22.7 Kg/hr (50 lb/hr)—this production rate being found essential for a commercially economic system It is only the foregoing discovery, namely that the cutter described in the system of the foregoing '452 application did not produce the fragments in the desired size range for most efficiently feeding the micronizer, that gave rise to the unique situation which requires committing the rope in a particular range of diameters at an economical rate using a better system.

This novel and improved rope handling system is designed and constructed because it was discovered that a rotary blade cutter of different construction could extend the limit of how small the tiny fragments could be made before they were fed to the micronizer, and that a different configuration of a train of pulleys (compared to that of the '452 system) provided a more efficient and economical system.

Moreover, as disclosed in the '452 application, it was found that when cellulose fiber rope is exposed to electron beam radiation to receive a dosage in the range from about 30 to 100 MegaRads, the rope is degraded so as to require controlling the tension under which it is uncoiled from a spool before it is chopped up. The term "chopped up" is used to refer to fragments generated by the action of a rotary blade cutter as opposed to the term "micronized" which is used herein to refer to particles or granules generated by the action of the micronizer. It is to be noted that the micronizer does not have blades but relies on the energy of high pressure air to cause fiber fragments to collide with each other at such high velocity as to break them up into even smaller fragments referred to as "granules". When a mass of naturally occurring relatively long cellulose fibers longer than about 6.35 mm (0.25") is fed directly to the micronizer, it typically generates fragments more than 75% of which are no shorter than 70 μm (micrometers or microns) even if the micronizer is allowed to run for an optimum period to generate these small fragments. When such long natural cellulose fibers are micronized beyond the optimum period, the fibers form a matte in the mill, and cannot be reduced to a smaller size. Such small fragments about 70 μm long, or longer, are used to enhance the function of drilling mud currently used in down hole drilling fluids in oil rigs and the like. When substrate is removed from a down hole, pumping clay into the down hole lowers the viscosity of the substrate and clay suspension as it flows through a discharge pipe. The combination of clay and cellulose fibers maintains the removed substrate as a suspension while maintaining a desirably low viscosity.

Because the rotary blade cutter used herein converts rope fed to it into granules, it is referred to as a "granulator". However, it is to be noted that it is a commercially available machine identified as a Model 811 Series Inline Granulator (available from Precision Airconvey Corporation) driven by a direct drive 5 HP motor at 1750 RPM, which machine is conventionally used to shred scrap synthetic resinous film typically less than 50.8 μm (2 mils) thick, into small strips which can be recycled. It is used herein by adjusting the edge of a stationary bed knife to be uniformly spaced at a cutting clearance no more than 25.4 μm (0.001"), preferably 12.7 μm (0.5 mil 0.0005") or less, from the edges of plural rotatable blades, so that the cellulose fibers are chopped into tiny fragments, the closer the cutting clearance, the smaller the length of the fibers. It is found that by equipping the machine with a screen having either a 6.35 mm (0.25") or 3.18 mm (0.125") mesh openings, either fragments no longer than 6.35 mm or 3.18 mm respectively, may be allowed to pass through the screens, the remaining longer fragments being chopped up into smaller ones until they pass through the screen chosen.

SUMMARY OF THE INVENTION

A system for committing rope comprises a rope-supplying means having a variable speed drive for uncoiling rope having a critical diameter in the range from 6.35 mm (0.25") to 19 mm (0.75") and means for continuously feeding it sequentially to a dancing roll and a variable speed feeder-pulley (also referred to as a feed roll) over which the rope is frictionally held so it does not slip as it is fed to a rotary blade committing means. The system includes means for maintaining a chosen tension less than that required to break the rope (less than the rope's breaking point) and means for continuously presenting an end of the rope to an inline granulator to be chopped into very small sections of fiber having a length in the range from 3.18 mm (0.125") to 6.35 mm (0.25"), preferably into tiny fragments less than 3.18 mm (0.125"), the granulator being fitted with a screen having openings no larger 6.35 mm, preferably 3.18 mm, so that more than 90% by weight of sieved fibers are in the range from about 2 μm to 700 μm (27.5 mils) with about 50% by weight of the fibers committed having an average length of about 32 μm. More preferably, the chopper is operated to provide more than 90% of the fibers shorter than 50 μm, the fragments having a median value (that is, 50% of the fragments are larger, and 50% are smaller) in the range from about 10-20 μm, and a mean value in the range from 1.2-25 μm.

Rope having a diameter in the above-identified range has a higher tensile strength (work load limit, before breaking) than rope of the same diameter which has been irradiated and received a dosage in the aforementioned dosage range. The non-irradiated rope has a work load limit in the range from about 91 Kg (200 lb) to 545 Kg (1200 lb) depending upon its diameter, the number of yarns used to twist the rope, whether twisted, solid braided or double braided, the particular fiber from which the rope is made, temperature, humidity and other factors. It is critical that the combination of rope-supplying means, dancing roll and variable speed feeder-pulley, maintain tension on the rope which tension is preferably at least 10% lower than the breaking point of the rope; and, that the rope be fed to a revolving blade cutter, as in an inline granulator, and that it be fitted with a screen with openings no larger than 6.35 mm (0.25").

A method for chopping rope made of cellulose fibers into very small fragments comprises, rotatably mounting a spool on a shaft for rotation about a transverse axis in a generally horizontal plane, to enable rope which is coiled on the spool to be uncoiled in a generally longitudinal direction; training the rope over a feeder-pulley adapted to frictionally engage the rope in non-slipping engagement therewith, the feeder-pulley being mounted for rotation about a transverse axis in a horizontal plane; control means to control the rotational speed of the feeder-pulley; training the rope over a train of pulleys positioned between the shaft and the feeder-pulley, the train including a dancing roll movable between at least two limit switches, one upper and one lower; controlling the speed of rotation of the shaft with a control means responsive to the upper and lower limit switches; feeding the rope into an inline granulator having a bed blade adjustable to provide a cutting clearance no more than 25.4 μm (0.001"), preferably 12.7 μm (0.0005") and most preferably 6.35 μm (0.00025"), with associated blades revolving at from about 1200 to 1800 revs/min; and fitting the granulator with a screen having openings no larger than 6.35 mm (0.25").

More particularly, operation of the system requires that a variable speed feeder-pulley frictionally engage the rope so that there is no discernible slippage, and feed the rope at a linear speed in excess of that required to deliver 22.7 Kg/hr (50 lb/hr) of rope to a granulator, preferably in the range from about 30.48 meters/min (100 ft/min) to 91.44 m/min (300 ft/min) depending upon the diameter of the rope and the cellulose fiber from which the rope is made. The speed of the variable speed roll is controlled by a potentiometer and proximity switch which reads the number of revolutions/minute the feed roll makes. The feed roll is then calibrated to convert its rotation into lb/hr of rope fed to the granulator. When the spool is small, that is has a weight of less than 113.6 Kg (250 lb) it may be free-turning, the rotation of the variable speed feed roll providing the tension required to uncoil the rope from the spool. However, when the spool is larger than 113.6 Kg (250 lb), the speed of rotation of the spool is controlled by a variable speed motor which allows the rope to be uncoiled at substantially the same linear speed as the rope being drivingly engaged by the variable speed roll. A dancing roll is employed between the spool and the variable speed feed roll to ensure the linear speed of rope being uncoiled from the spool matches the linear speed of the rope being delivered by the variable speed feed roll.

BRIEF DESCRIPTION OF THE DRAWING

The foregoing and additional objects and advantages of the invention will best be understood by reference to the following detailed description, accompanied with schematic illustrations of preferred embodiments of the invention, in which illustrations like reference numerals refer to like elements, and in which.

DETAILED DESCRIPTION OF THE INVENTION

Figure 1:
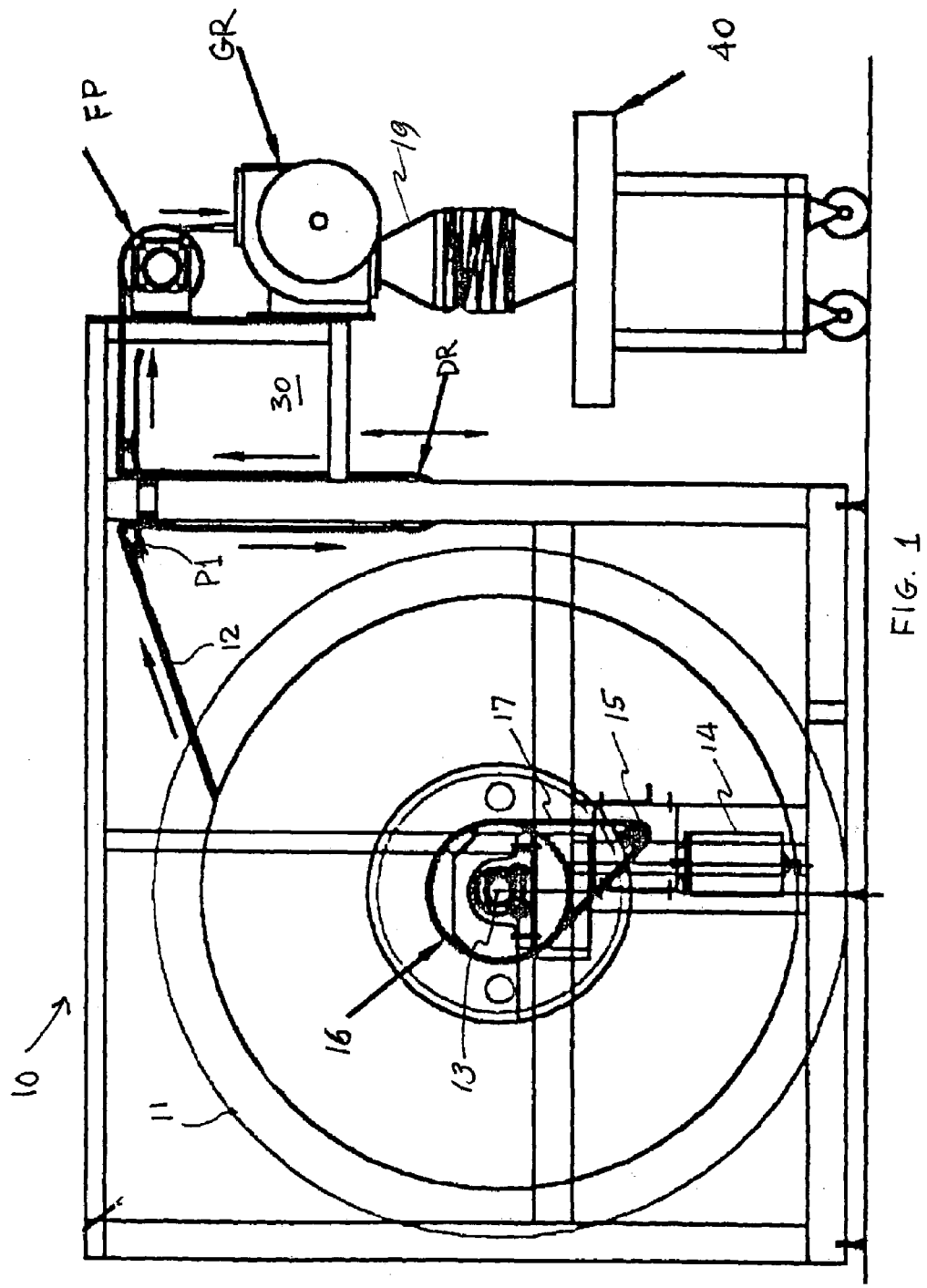
FIG. 1 is a side elevational view of the machine illustrating a large spool of rope from which it is fed sequentially to plural pulleys including a dancing roll before the rope passes over a variable speed feed roll and enters a granulator.
Figure 2:
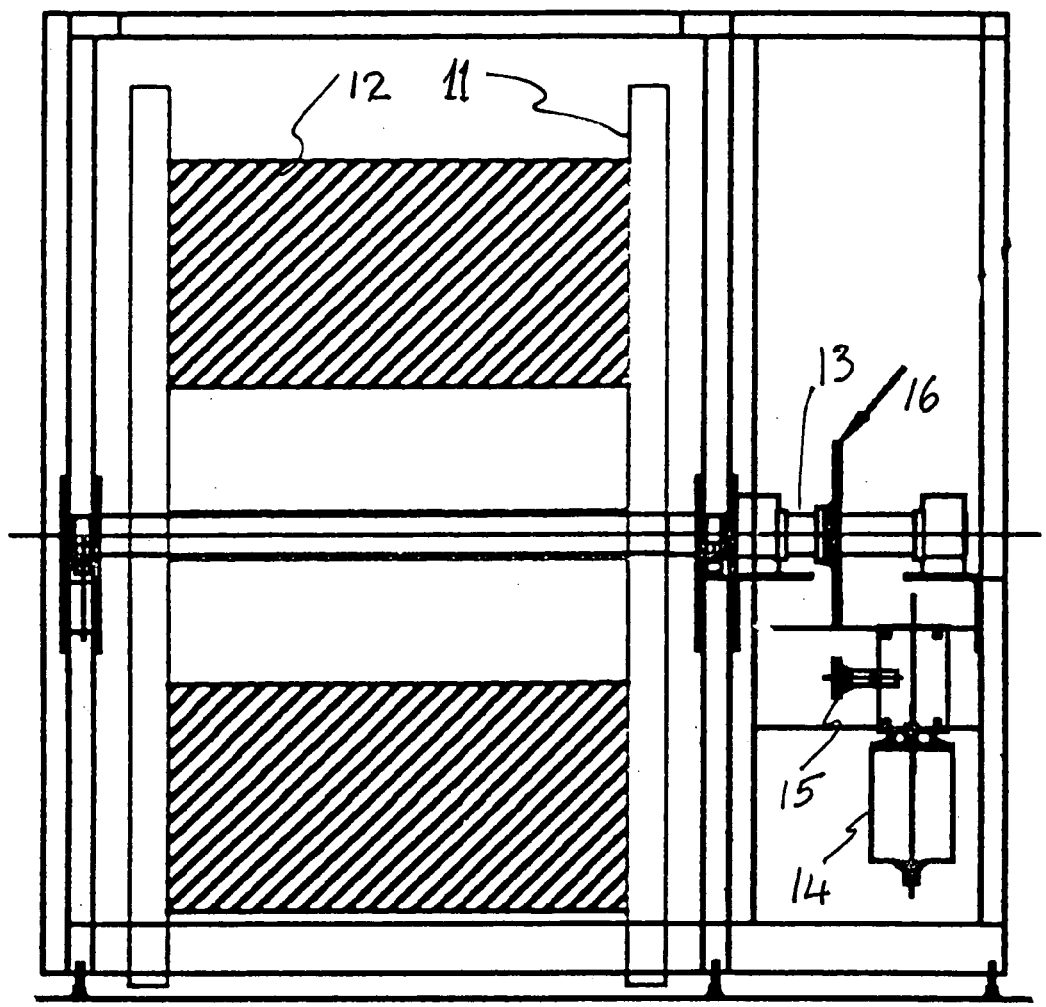
FIG. 2 is an end elevational view from behind the spool illustrating the drive mechanism for rotating the spool and uncoiling the rope from the spool.
Figure 3:
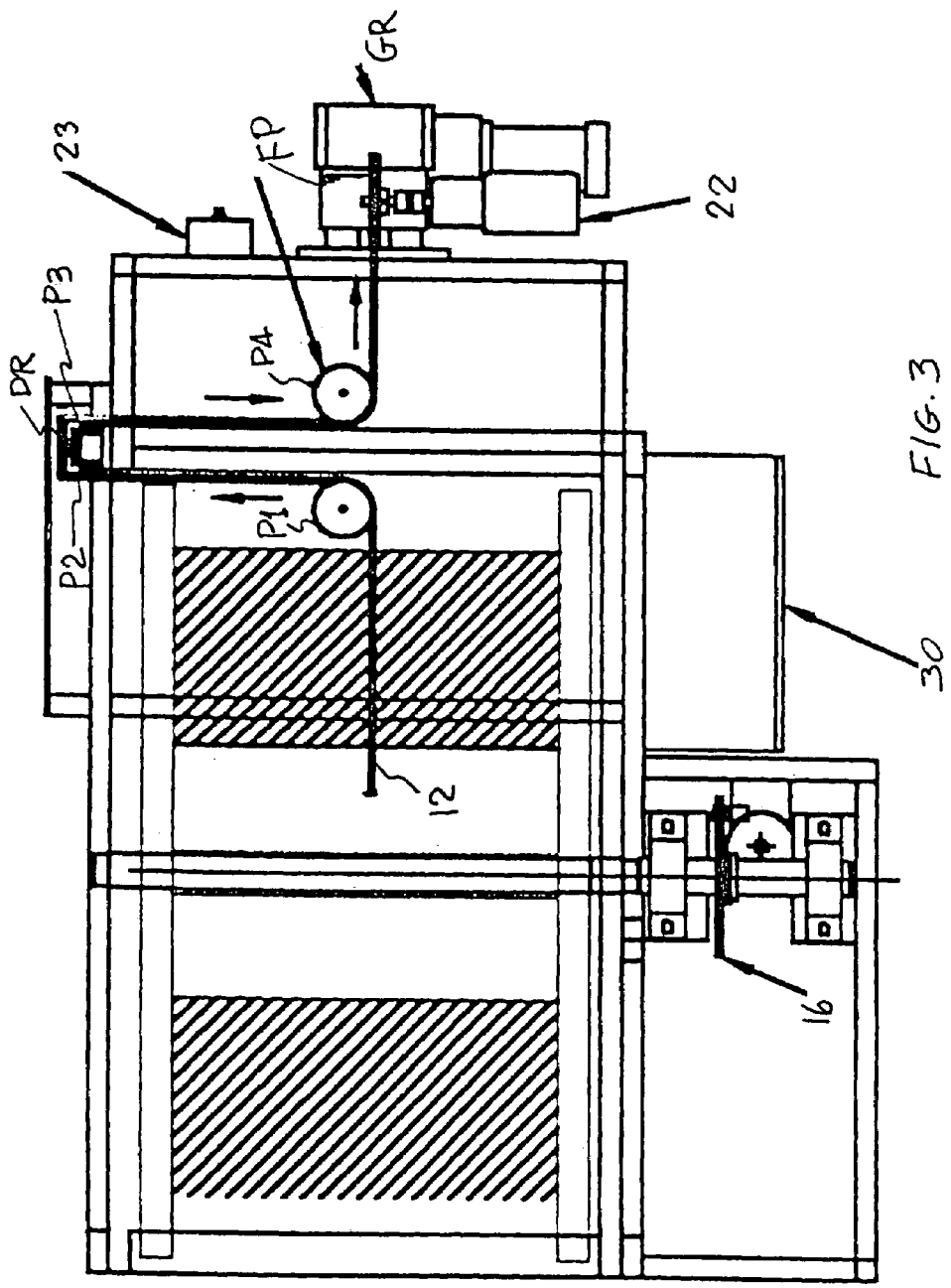
FIG. 3 is a top plan view of the machine.
Figure 4:
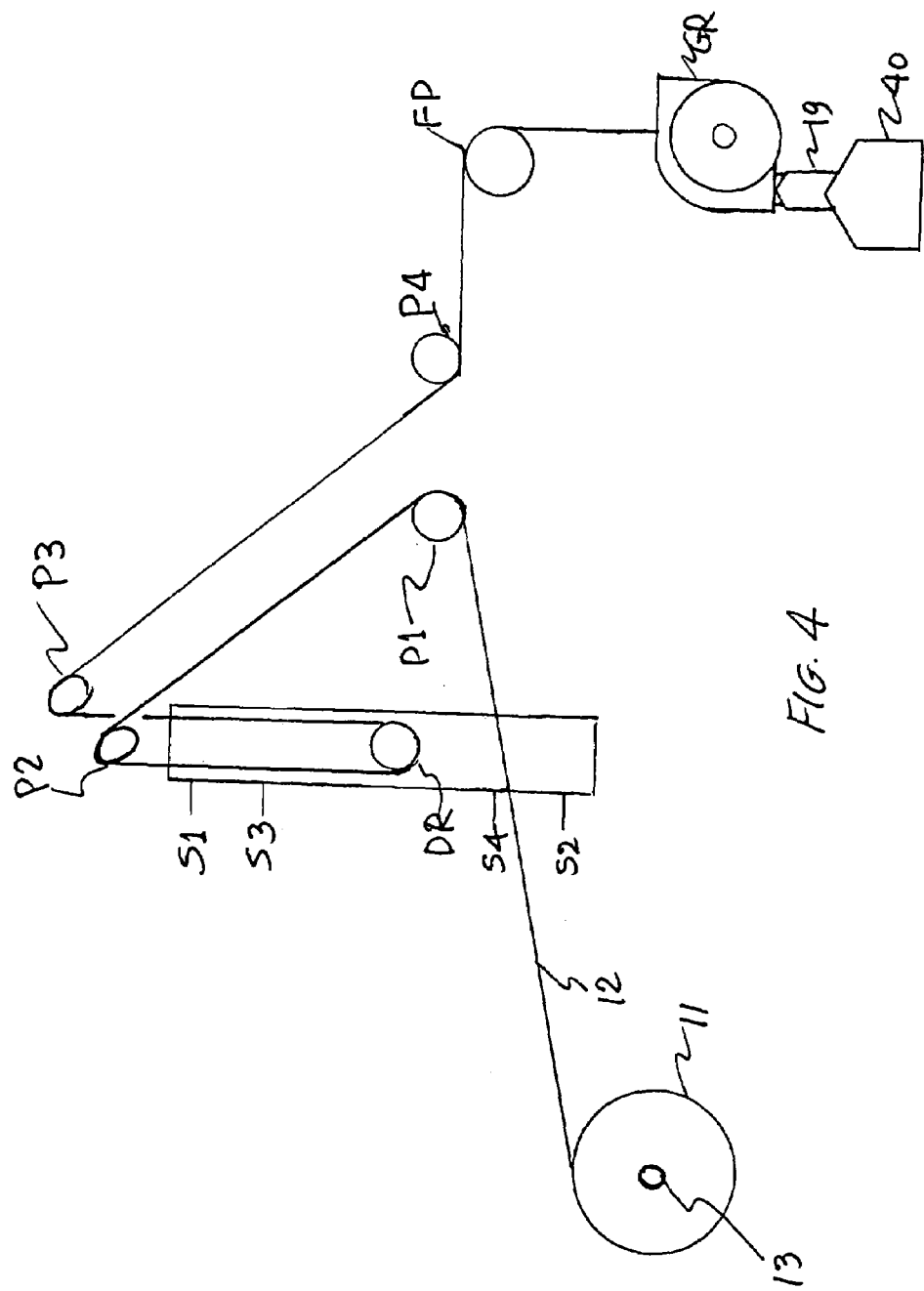
FIG. 4 is a perspective view schematically illustrating the relative positions of the plural pulleys in the train, which pulleys are disposed intermediate the spool and the variable speed feed roll.

Currently, naturally occurring relatively long cellulose fibers are committed, as described in the '452 application, into particles having a length in the range from about 3.2 mm (0.125") to 6.35 mm (0.25"). Prior to the '452 application, the natural fibers, typically first washed and optionally bleached if a white fiber is desired, were fed as small squares to a micronizing mill ("micronizer") such as a Model 30 Roto-Jet manufactured by Fluid Energy A1-Jet Company, as disclosed in the '712 patent, or a Model 24. This jet mill, which is a high speed grinding mill with an integral, independently driven dynamic classifier, is operated with a flow rate of 800-2000 CFM, preferably 1500-2000 CFM air at 120 psi, depending upon the mill chosen, inter alia, and produces particles distributed in a narrow size range, that is, typically, at least 90% by weight of the micronized particles are less than 25 μm, preferably less than 10 μm in length, and the average length of all particles is in the range from about 9 μm-15 μm, preferably 4 μm-5 μm, as measured in a Microgram Standard Range Particle Analyzer.

Such relatively long natural or physically unmodified fibers, when fed to the micronizer which is operated for long enough to obtain particles having the minimum average length under micronizing conditions, results in particles having a minimum average particle length no smaller than about 70 μm. Particles or fragments of cellulose fibers 70 μm long or longer are outside the aforementioned narrow range of lengths for micronized particles.

Preferred cellulose fibers are cotton, jute, manila, sisal and hemp, and blends of one with another, all of which are widely used to make rope. The diameter of the rope is not narrowly critical, being dictated in large part by the economics of providing the optimum dosage to obtain the desired frangibility of the fibers without deleteriously degrading them. Most preferred is cotton rope having a diameter in the range from about 9.5 mm (0.375") to 12.7 mm (0.5") which is spooled on a large spool having a diameter in the range from about 1 meter (39.37") to 2 m (78.74") and carrying in the range from about 304.8 m (1000 ft) to 15240 m (50,000 ft) of rope depending upon the diameter.

The design and construction of the rope-on-spool uncoiler and granulator system described herein was driven by the necessity to supply tiny fragments of cellulose fibers to the substantial exclusion of longer fragments, because tiny fragments fed to the aforementioned commercially available micronizer yielded an economic production rate. Such tiny fibers resemble generally elongated grain-shaped primary particles referred to as "granules" having a length in the range from about 0.1 mm (0.004 in) but less than 3.175 mm (0.125 in). Stated differently, the throughput of micronized fragments from the micronizer can be greatly increased if the feed to the micronizer is pre-fragmented. Using commonly available rope is the most convenient way of providing the tiny fragments as long as the tension on the rope is less than that required to break it. If the rope is irradiated and the fibers chemically and/or physically weakened then even greater care is to be exercised so as not to break the rope while it is being fed to a granulator.

The unique situation addressed in the '452 application, and herein, occurs when such rope in a critically small diameter in the range from 0.25" to 0.75" is deliberately irradiated with sufficient energy to weaken the physical and chemical bonds in the cellulose fibers from which the rope is made, with the specific purpose of committing the irradiated rope which is rendered frangible. The diameter of the rope is critical because larger diameters are not readily susceptible to receiving a requisite dosage of irradiation, should weakened fibers be desired.

The structural elements of the system and the method of its operation are the same for any rope which is to be committed. When the rope to be committed has not been irradiated, its tensile strength is typically at least double its tensile strength after it has been irradiated for the specific purpose of providing particles smaller than 70 μm. As stated above, such non-irradiated rope may be committed into primary particles having a minimum average length of about 70 μm with a much higher setting for tension than that required for committing irradiated rope as there is a much lower risk of the breaking the non-irradiated rope. In other respects operation of the machine is the same as that for irradiated rope.

Irradiation of the rope is done under conditions of electron beam irradiation generally disclosed in the '712 patent and the parent '452 application the disclosures of which are incorporated by reference thereto as if fully set forth herein. Irradiation is preferable when fiber fragments having an average length smaller than about 10 μm are desired. The method of irradiating rope forms no part of this invention.

Referring to the FIGS. 1-4 illustrating the system referred to by reference numeral 10, and particularly to FIG. 1, there is shown a large spool 11, about 2 m (6 ft) in diameter, on which about 300 Kg (660 lb) of rope 12, 12.7 mm (0.5") in diameter, is coiled. The spool is non-rotatably mounted on a shaft 13 inserted in a central transverse bore of the spool, and the shaft can be rotated by a variable speed motor 14 which turns a small sprocket 15, and in turn a large sprocket 16 fixedly mounted on the shaft 13, with a chain 17 drivingly trained on the sprockets. The variable speed motor 14 is thus drivingly engaged with the shaft 13 by means for doing so, whether such means comprises sheaves and a drive belt, a chain and sprockets, or a directly engaging worm gears secured to the motor 14 and shaft 13. The speed of rotation of the motor is determined by an electrical input from two pairs of limit switches, a pair of upper and lower limit switches S1 and S2 at the extreme upper and lower limits of travel of a floating or dancing roll DR, the switches being mounted on a vertical panel adjacent the dancing roll DR; and a pair of intermediate limit switches, also mounted on the panel 20, between the extreme limits, namely upper intermediate switch S3 and lower intermediate switch S4 (see FIG. 4). In operation, electrical inputs from the intermediate switches S3 and S4 provide small corrections in rotational speed of the shaft 13 to maintain the position of the dancing roll DR between S3 and S4. Movement of the dancing roll to the extreme limits triggering S1 or S2 produce large corrections in rotational speed of the shaft 13.

The spool 11 is rotated clockwise as seen in this side view, so that the rope 12 is uncoiled in the longitudinal direction as shown by the arrow, as the rope is trained over a first pulley P1 rotatable about a vertical axis, then over a second pulley P2 rotatable about a longitudinal axis so that the rope 12 is directed vertically downwards to the dancing roll DR rotatable about a transverse axis. After being trained around DR the rope 12 is directed vertically upwards to pulley P3 disposed in mirror image relationship with pulley P2 and similarly rotatable about a longitudinal axis so that the rope is directed along the transverse axis to pulley P4 disposed in mirror image relationship with pulley P1 and similarly rotatable about a vertical axis so that the rope 12 is directed along the longitudinal axis to a calibrated feeder-pulley FP which directs the rope downwards into the granulator GR. The speed of rotation of FP is controlled by a variable speed motor 22 which is calibrated to deliver a specified weight of rope per unit time and controlled by a speed control unit 23.

The sides of the groove in feeder-pulley FP are provided with serrations to frictionally engage the rope and keep it from slipping. To ensure that the rope does not slip, a spring-loaded pressure bar (not shown) is biased against the rope 12 as it is fed around the feeder-pulley FP. The speed of rotation of the feeder-pulley FP is set, that is, maintained constant at a chosen speed, so that the operator will choose the rate of feed to the granulator, which rate is converted to the corresponding linear speed of the rope 12.

The switches S1 and S2 sense the limits of upper and lower travel of the dancing roll DR and the rotational speed of the of the spool 11 is adjusted to maintain the position of the dancing roll DR between the switches, while the rotational speed of the feeder-pulley FP is kept constant. The input from the feeder-pulley FP also adjusts the speed of the variable speed motor 13 to match the linear speed of the rope to feeder pulley FP. The controls for the system are housed in a control panel 30.

To avoid writing a program for continuously varying the rotational speed of the spool 11 while maintaining the speed of feeder-pulley FP constant, the switches S1, S2, S3 and S4 are set to correspond to specific rotational speeds of the spool. Should the dancing roll DR traverse the limits between the intermediate limit switches S3 and S4 where it is desirably held, and trip either S1 or S2, the rotation of spool 11 either speeds up or slow down rapidly to return the dancing roll DR to its position between the intermediate switches S3 and S4.

The granulator GR is equipped with an internal screen (not shown), as stated above, and it is essential that the adjustable bed knife be set for a clearance of 12.7 μm (0.0005" or 0.5 mil). Fragments longer than 3.18 mm (0.125") are swept from the screen and recycled to the revolving blades of the granulator until they are small enough to pass through the sieve openings.

When the fragments pass through the screen openings they are collected in a large diameter duct which exerts a vacuum on the screen to suck the fragments through its openings and into the inlet of the micronizer 40 where the fragments are further committed into micron-sized portions. The vacuum is exerted by directing a portion of a stream of high pressure air fed to the micronizer to a nozzle beneath the screen of the granulator.

One skilled in the art will appreciate that setting the adjustable bed blade at a spacing greater than 0.0005" will result in relatively longer tiny fragments than the ones deemed optimum herein, as will using a sieve with openings larger than 0.125", and such longer tiny fragments will, in turn, result in slightly larger micronized particles if micronized under the same conditions as the smaller tiny fragments; however, larger micronized particles are generally not desirable.

When the pre-fragmented tiny fragments are then micronized, more than 90% of the micronized particles are smaller than about 25 μm, preferably smaller than 10 μm, having a median value in the range from about 8-12 μm and a mean value in the range from about 9-15 μm.

It will be appreciated that since it was found that tiny fragments generated in the inline granulator are peculiarly well-suited to being micronized in the desired narrow size range, they are typically directly ducted to the intake of the micronizer 40 through a conduit 19 in which air jet generates a vacuum under the screen of the granulator GR.

Having thus provided a general disclosure of the relevant subject matter and described the system in detail, and illustrated the invention with a specific embodiment of the best mode of making and using the invention, it is to be understood that no undue restrictions are to be imposed by reason of the specific embodiment illustrated and described, and particularly, that the invention is not restricted to a slavish adherence to the details set forth herein.

We claim:

1. A system for chopping rope of cellulose fibers into fragments, comprising,
    a spool having rope coiled thereon, the spool being fixedly disposed on a rotatable shaft, the rope having a diameter in the range from 3.175 mm (0.125") to 19.05 mm (0.75");
    a variable speed drive means drivingly engaged with the shaft to rotate it at a chosen number of revolutions per unit time;
    a variable speed feeder-pulley over which the rope is trained in non-slipping engagement therewith;
    control means to control the revolutions per minute of the feeder-pulley within a predetermined range;
    a train of pulleys over each of which the rope is engaged, the pulleys disposed intermediate the shaft and the feeder-pulley, the train including a dancing roll movable between upper and lower limits;
    limit switch means to sense the upper and lower limits of travel of the dancing roll;
    an inline granulator having a bed blade adjustable to provide a cutting clearance of no more than 25.4 μm (0.001") and associated blades revolving at a speed in the range from about 1200-1800 revs/min; and,
    a screen means having openings no larger than 6.35 mm (0.25").

2. The system of claim 1 wherein the cutting clearance is no more than 12.7 μm (0.0005") and the openings in the screen are no larger than 3.18 mm (0.125") and more than 90% by weight of sieved fibers are in the range from about 2 μm to 700 μm (27.5 mils).

3. The system of claim 1 wherein the dancing roll is movable between at least an extreme upper limit switch and an extreme lower limit switch, and each switch is operatively connected to a control unit adapted to control the speed of rotation of the shaft.

4. The system of claim 3 wherein the dancing roll is additionally movable between an intermediate upper limit switch and an intermediate lower limit switch, and each switch is operatively connected to the control unit adapted to control the speed of rotation of the shaft.

5. The system of claim 1 including a conduit in open fluid communication with the granulator's discharge the conduit having an air jet means therein to generate a vacuum at the discharge of the granulator; and,
    a micronizer having an intake in open fluid communication with the conduit.

6. A method for chopping rope made of cellulose fibers into fragments smaller than 6.35 mm (0.25"), comprises,
    rotatably mounting a spool on a shaft for rotation about a transverse axis in a generally horizontal plane, to enable rope which is coiled on the spool to be uncoiled in a generally longitudinal direction;
    training the rope over a feeder-pulley adapted to frictionally engage the rope in non-slipping engagement therewith, the feeder-pulley being mounted for rotation about a transverse axis in a horizontal plane;
    controlling the rotational speed of the feeder-pulley;
    training the rope over a train of pulleys positioned between the shaft and the feeder-pulley, the train including a dancing roll movable between at least two limit switches, one upper and one lower;
    controlling the speed of rotation of the shaft with a control means responsive to the upper and lower limit switches;
    feeding the rope into an inline granulator having a bed blade adjustable to provide a cutting clearance no larger than 25.4 μm (0.001") with associated blades revolving at from about 1200 to 1800 revs/min; and,
    fitting the granulator with a screen having openings no larger than 6.35 mm.

7. The method of claim 6 including sensing movement of the dancing roll at an intermediate upper limit switch and an intermediate lower limit switch, and adjusting the cutting clearance to be no larger than 12.7 μm (0.0005").

8. The method of claim 7 including adjusting the cutting clearance to be no larger than 6.35 μm (0.00025").

9. The method of claim 6 including exerting a vacuum at the granulator's discharge, and directly flowing the fragments to a micronizer.

* * * * *